United States Patent [19]
Guadagno et al.

[11] Patent Number: 5,512,157
[45] Date of Patent: Apr. 30, 1996

[54] ELECTROPHORESIS PLATE

[75] Inventors: Philip A. Guadagno, Vidor; Rajani Rayachoti; Eric H. Petersen, both of Beaumont, all of Tex.

[73] Assignee: Helena Laboratories Corporation, Beaumont, Tex.

[21] Appl. No.: 361,702

[22] Filed: Dec. 22, 1994

Related U.S. Application Data

[63] Continuation of Ser. No. 86,918, Jul. 7, 1993, abandoned, which is a continuation-in-part of Ser. No. 79,228, Jun. 21, 1993, abandoned.

[51] Int. Cl.$^6$ .................... G01N 27/26; G01N 27/447
[52] U.S. Cl. .................................. 204/616; 204/470
[58] Field of Search ................... 204/299 R, 182.8, 204/180.1

[56] References Cited

U.S. PATENT DOCUMENTS

| | | | |
|---|---|---|---|
| 3,674,678 | 7/1972 | Post, Jr. et al. | 204/299 R |
| 4,360,418 | 11/1982 | Golias | 204/299 R |
| 4,391,689 | 7/1983 | Golias | 204/299 R X |
| 4,810,348 | 3/1989 | Sarrine et al. | 204/299 R |
| 4,827,780 | 5/1989 | Sarrine et al. | 204/182.8 X |
| 4,844,786 | 7/1989 | Sugihara et al. | 204/299 R |
| 4,874,491 | 10/1989 | Stälberg | 204/182.8 |
| 4,890,247 | 12/1989 | Sarrine et al. | 204/182.8 X |
| 4,892,639 | 1/1990 | Sarrine et al. | 204/299 R |
| 4,909,920 | 3/1990 | Sarrine et al. | 204/299 R |
| 4,938,080 | 7/1990 | Sarrine et al. | 204/299 R X |
| 4,954,237 | 9/1990 | Sarrine et al. | 204/299 R |
| 4,963,243 | 10/1990 | Ogawa et al. | 204/299 R |
| 4,975,173 | 12/1990 | Tansamrit et al. | 204/299 R |
| 4,999,340 | 3/1991 | Hoffman et al. | 514/23 |

OTHER PUBLICATIONS

B. G. Johansson & J. Stenflow, "Polyacrylamide Slab Electrophoresis Followed by Electrophoresis into Antibody--Containing Agarose Gel" Analytical Biochemistry 40 (1971) 232–236.

Bengt G. Johansson & Stellan Ajertén, "Electrophoresis, Crossed Immuno-electrophoresis; and Isoelectric Focusing in Agarose Gels with Reduced Electroendosmotic Flow" Analytical Biochemistry 59 (1974) 200–213.

Hans-Christoph Weise et al "Isoelectric Focusing and Immunoprecipitation on Slabs of Agarose" Progress in isoelectric focusing and isotechoporesis, Editor: P. G. Righetti (No month available 1975) 93–98.

Primary Examiner—John Niebling
Assistant Examiner—John S. Starsiak, Jr.
Attorney, Agent, or Firm—Dorsey & Whitney

[57] ABSTRACT

An electrophoresis plate includes a substrate and an electrophoresis medium layer on the substrate. The electrophoresis plate may be used for medical testing by placing fluid specimens in wells on the electrophoresis medium layer so that the specimens can be separated into different fractions by applying an electric field across the electrophoresis medium layer. The electrophoresis medium layer includes liquid in a microporous gel such as agarose. The electrophoresis plate is packaged with a protective plastic film across the electrophoresis medium layer, but removal of the protective film prior to use of the electrophoresis plate leaves liquid that has been expressed from the electrophoresis medium layer on the surface of the electrophoresis medium layer. A surfactant such as methyl cellulose is included in the electrophoresis medium layer so that the expressed liquid will wet the electrophoresis medium layer in a uniform film instead of forming irregular pools or patches which would have to be removed before the electrophoresis plate is used.

26 Claims, 2 Drawing Sheets

ELECTROPHORESIS PLATE

This application is a Continuation of application Ser. No. 08/086,918, Filed Jul. 7, 1993, which is a continuation-in-part of application Ser. No. 08/079,228, filed Jun. 21, 1993. The disclosure of this parent application is incorporated herein by reference.

BACKGROUND OF THE INVENTION

The present invention is directed to an electrophoresis plate, and more particularly to an electrophoresis plate which is packaged with a plastic film on it.

Valuable information can be obtained by an analysis of certain biological fluids from a patient, such as blood serum, when diagnosing the patient's illness. Electrophoresis is known to be an effective technique for separating the various components of such fluid for subsequent analyses using optical densitometry techniques. The physical phenomenon underlying electrophoretic analysis is that particles which have an effective electric charge and which are deposited on a solid or semi-solid medium are caused to move with respect to the medium by an electric field applied across the medium. Particles of different types move at different rates, so a mixture of different types of particles is separated into its different components or fractions by electrophoretic analyses. These separated fractions may then be stained (visualized) by exposing them to a suitable reagent so that the fractions can be optically detected using visible or ultraviolet light.

The electrophoresis process has been performed through a series of manual steps for many years. The manual process typically has started with the operator preparing an electrophoresis chamber by filling appropriate cavities of the chamber with buffer solution. Buffer solution is a liquid used in the electrophoresis process to provide an electrical interface to a power source so that an electric field may be applied to the medium and to contribute to maintaining the surface of the electrophoresis medium in a moist condition. The electrophoresis medium is typically a gel substance such as agarose that has been fixed onto a suitable substrate (e.g., Mylar) to form an electrophoresis plate. The liquid sample to be examined is typically blood serum, but of course may be other liquids.

After the operator has prepared the electrophoresis chamber, he then applies appropriate sample volumes to precise locations on the electrophoresis medium. The operator then places the medium into the electrophoresis chamber so that the edges of the medium are immersed in two buffer cavities at each of its longitudinal ends. Electrophoresis is then performed using a precise and consistent voltage differential applied for a precise and consistent interval of time across the buffer cavities and therefore the complete surface.

After electrophoresis has been completed, the operator applies a uniform coating of a development reagent to the surface of the medium, allowing a precise and consistent interval of time for the reagent and sample to chemically react. The development reagent is a liquid used after electrophoresis to chemically react with the separated fractions of the fluid sample, causing the fractions to exhibit optical characteristics.

Next, the operator places the electrophoresis medium into a temperature-controlled oven and incubates it using a precise and consistent temperature and time interval. Incubation is the process of controlling the chemical reaction between the fractions of the liquid sample and the development reagent by means of applying heat for a fixed interval of time.

Next, the operator dries the electrophoresis medium by increasing the oven temperature for a second precise and consistent temperature and time interval. The drying process stops the reaction between the separated fractions and the reagent by removing water from the medium. The medium can then be examined using optical densitometry techniques to determine which fractions were present in the original samples and to find their relative proportions.

The manual process described above requires careful attention by the operator in order to provide accurate and reproducible results. It is therefore not surprising that techniques for performing electrophoresis automatically have been developed. For example, U.S. Pat. Nos. 4,360,418 and 4,391,689 to Golias describe an automated electrophoresis and staining apparatus and method. U.S. Pat. Nos. 4,810, 348, 4,890,247, 4,909,920, and 4,954,237 to Sarrine et al also describe an automated electrophoresis apparatus and method. An automated applicator assembly with pipettes for transferring samples to the electrophoresis medium during automatic analysis is described in U.S. Pat. Nos. 4,827,780 and 4,938,080 to Sarrine et al. All of these patents, which are assigned to the assignee of the present invention, are incorporated herein by reference.

Electrophoresis plates for use with automatic equipment are typically distributed with plastic films over the working portion of the electrophoresis medium layer. The film protects the working portion from contaminants and also prevents evaporation of water and thus helps to maintain the integrity of the electrophoresis medium layer during storage. This film must be removed by the operator before the fluid samples are deposited on the electrophoresis medium layer.

The electrophoresis plate is typically made by placing a substrate in a mold and injecting a thermosetting gel. The gel has a liquid component which includes water, a buffer, and frequency additional substances. For example, in the past surfactants such as tritons have been included in the liquid to produce better separation of the samples and to improve resolution and stability. The protective film is applied to the electrophoresis medium layer after the completed electrophoresis plate has been removed from the mold, and soon thereafter the electrophoresis medium layer begins to expel or express a small portion of the liquid in the gel due to a phenomenon known as syneresis. The expressed liquid accumulates in a layer between the surface of the electrophoresis medium layer and the protective film and is retained there by capillary action.

When the operator of the automatic electrophoresis equipment removes the protective film, the accumulated liquid forms thin, irregular patches or pools on the surface of the electrophoresis medium layer. Since the liquid is electrically conductive these irregular patches provide irregular current paths and thereby keep the electrophoresis medium layer from being electrically homogeneous at its upper surface. For this reason it has been customary for the operator to remove the accumulated liquid by blowing it away, for example, or by blotting the electrophoresis plate against an absorbent surface.

Removal of the accumulated liquid by the operator increases the risk that the electrophoresis medium layer might become contaminated or that its integrity/uniformity might become compromised. Contamination by lint is a particular problem, since lint may carry brighteners which fluoresce under ultraviolet light and since automatic electrophoresis equipment typically employs ultraviolet light when reflectance densitometric techniques are used to read the separated proteins on the electrophoresis plate.

SUMMARY OF THE INVENTION

An object of the invention is to provide an electrophoresis plate which imposes a reduced demand on the time of the operator of automatic electrophoresis equipment and which additionally reduces the risk of contaminating the electrophoresis plate.

A more particular object is to provide an electrophoresis plate whose expressed liquid does not need to be removed by the operator after the protective film is peeled off.

Another object is to provide an electrophoresis plate which includes a surfactant in the electrophoresis medium layer to alter the surface tension of the expressed liquid with respect to the electrophoresis medium layer so that the liquid wets the upper surface of the electrophoresis medium layer in a uniform film after removal of the protective plastic film. Because the film of liquid is uniform rather than patchy,. it does not make the electrophoresis medium layer electrically non-homogeneous at its upper surface.

These and other objects which will become apparent in the ensuing detailed description can be attained by providing an electrophoresis plate which includes a substrate, and an electrophoresis medium layer on the substrate, the electrophoresis medium including water, a microporous gel in which the water is retained, and a surfactant selected from the group consisting of povidones and water-soluble celluloses in the water. Methyl cellulose has been found to be particularly satisfactory for use in an electrophoresis plate for assaying isoenzymes of creatine kinase.

DESCRIPTION OF THE PREFERRED EMBODIMENTS

Figure 1:
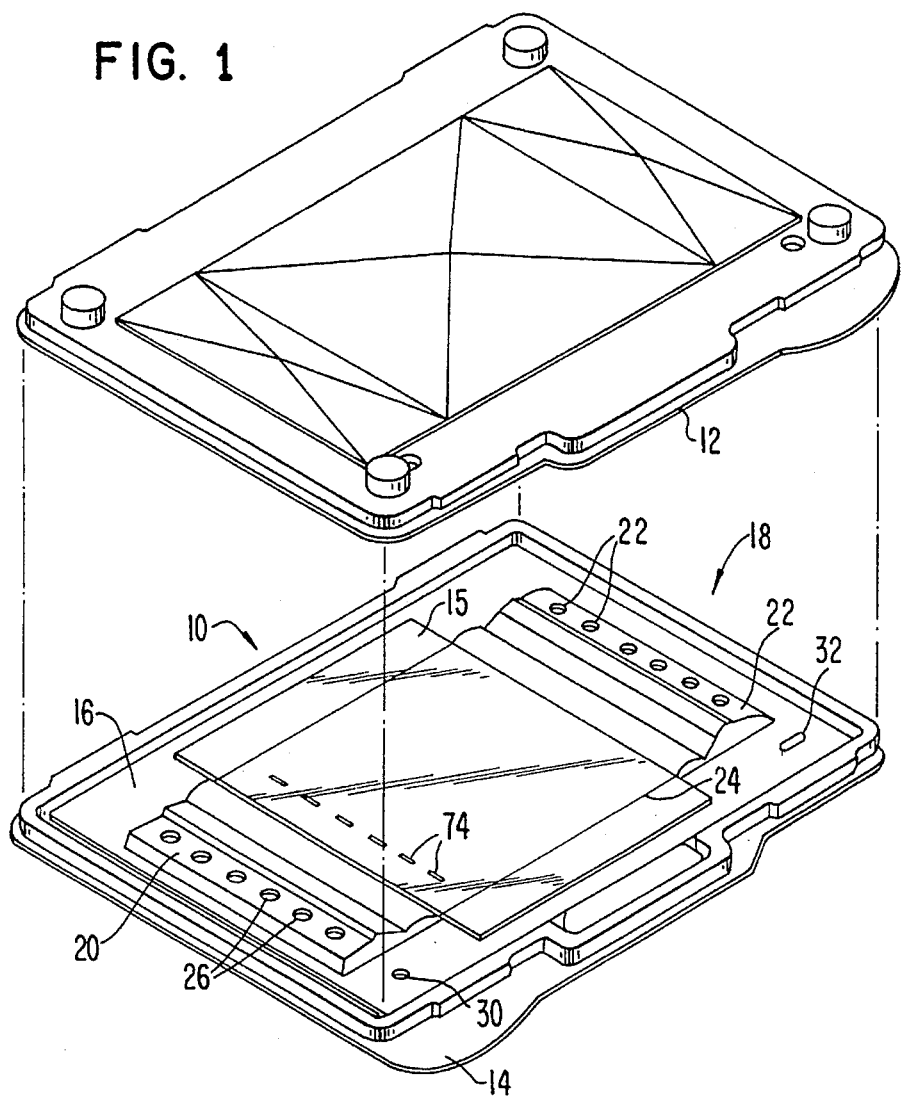
FIG. 1 is an exploded perspective view illustrating a completed electrophoresis plate in accordance with the invention packaged in a disposable clam-shell housing, and a removable plastic film protecting the central portion of the electrophoresis medium layer of the plate.

FIG. 1 illustrates an electrophoresis plate 10 in accordance with the present invention. Plate 10 is shown in its packaged state awaiting use, in a disposable clam-shell package formed by snap-together plastic container halves 12 and 14. A disposable Mylar (trademark) plastic film 15 protects the working surface of plate 10. Film 15 is two thousandths of an inch thick and has a thin coating of agarose on its lower surface. The arrangement shown in FIG. 1 is hermetically sealed in a pouch (not illustrated) for distribution to medical testing facilities.

Plate 10 includes a substrate 16 made, for example, from a thin Mylar (trademark) plastic sheet. Substrate 16 supports an electrophoresis medium layer 18 having a first end portion 20, a second end portion 22, and a central portion 24.

Electrophoresis medium layer 18 is a stiff gel whose composition will be described later, but for now it is noted that it contains liquid along with a microporous support medium such as agarose for the liquid. The term "microporous" means that the electrophoresis medium has tiny pores which hold the liquid, somewhat in the manner of an extremely fine-grain sponge.

End portion 20 of electrophoresis medium layer 18 has six holes 26 and, similarly, end portion 22 has six holes 28. Substrate 16 has an alignment hole 30 and an alignment slot 32. Although not shown in FIG. 1, substrate 16 also has six holes aligned with the holes 26 in end portion 20 and six holes aligned with the holes 28 of end portion 22.

From the above description of electrophoresis plate 10 it will be apparent that the term "plate" does not imply a rigid structure; instead, electrophoresis plate 10 is rather flexible.

Figure 2:
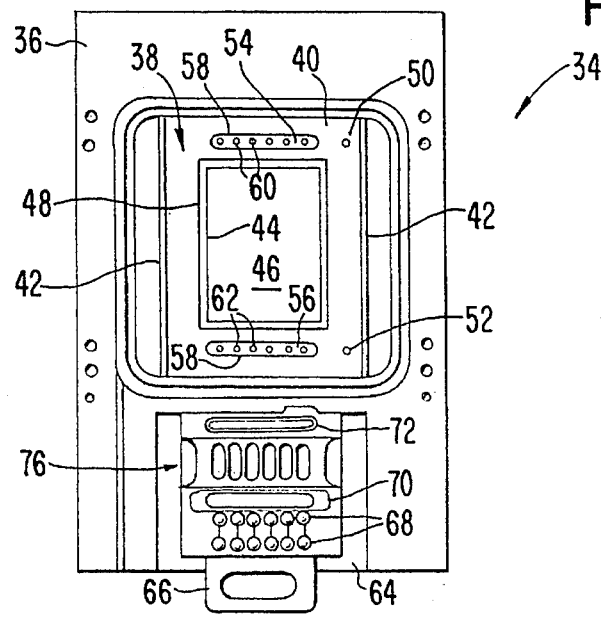
FIG. 2 is a top plan view of an electrophoresis platform with which the electrophoresis plate can be used.

FIG. 2 illustrates a top view of an electrophoresis platform 34 with which plate 10 can be used. Platform 34 includes a plastic tray 36 with a recessed region 38. A ceramic plate 40 is disposed in recessed region 28 between a pair of ribs 42 protruding from tray 36. Plate 40 has a central opening 44. A heat-transfer member 46 protrudes through opening 44 and has a top surface that is flush with the top surface of plate 40. A thin plastic film 48 is adhesively attached to the top surface of plate 40 and covers member 46.

Alignment pegs 50 and 52 extend from tray 36 through two holes (not numbered) in plate 40. Elongated conductive members 54 and 56 are mounted on tray 36 and are exposed through slots 58 in plate 40. Conductive member 54 has six electrodes 60 which extend upward through one slot 58 and conductive member 56 has six electrodes 62 which extend upward through the other slot 56.

Tray 36 also has a recessed region 64 for accommodating a removable sample tray 66. Tray 66 has two rows of sample wells 68, each row having six wells 68 as shown. Sample tray 64 also has troughs 70 and 72 for a cleaning solution and water to wash pipettes (not illustrated) of an applicator assembly (not illustrated) which transfers fluid specimens from one of the rows of wells 68 to corresponding wells 74 (see FIG. 1) molded into the central portion 24 of electrophoresis medium layer 18. A strip of paper (not illustrated) for blotting the pipettes during the washing procedure is deposited on region 76 of sample tray 66.

Typically a reference/calibrator fluid is placed in one of the wells 68 of a row, a normal control fluid is placed in another well 68 in the row, and an abnormal control fluid is placed in a further well 68 in the row. The remaining three wells 68 in the row are filled with samples collected from a patient at regular time intervals.

To conduct an assay, the operator removes electrophoresis plate 10 from the container and discards container halves 12 and 14. Plate 10 is placed in recessed region 38 so that the edges of substrate 16 engage ribs 42, alignment peg 52 extends through alignment hole 30, alignment peg 50 extends through alignment slot 32, electrodes 60 extend through holes 28, and electrodes 62 extend through holes 26. Film 16, which has protected central portion 24 of electrophoresis medium layer 18 up to now from lint and other contamination, is then removed by the operator. Samples are transferred from one of the rows of wells 68 to the wells 74 and electrophoresis is then conducted by supplying suitable voltages to conductive members 54 and 56 for a predetermined period of time. Thereafter a reagent is spread across plate 10 to cause the separated fractions to fluoresce under ultraviolet light, and a reflectance densitometric analysis is conducted after the plate has been incubated and dried to ascertain the relative proportions of the fractions present in the samples.

Further information about electrophoresis platform 34 is available in an application entitled "Platform For Conducting Electrophoresis, and Electrophoresis Plate For Use With the Platform" by Robert J. Sarrine, filed Jun. 21, 1993 under attorneys' docket HELAB 0296. The Sarrine application is assigned to the assignee of the present application and is incorporated herein by reference.

As was noted above in the "Background of the Invention" section, an inherent property of the electrophoresis medium is that an accumulation of liquid remains on the surface of central portion 24 when the operator removes protective film 15. In prior art electrophoresis plates this accumulated liquid forms thin, irregular patches or pools of liquid on the surface of the electrophoresis medium when film 15 is peeled off. It is conventional for the operator to remove the accumulated liquid before using a prior art electrophoresis plate since the liquid contains a buffer which serves as an electrolyte. Some of the electrophoresis current would flow through the liquid on the surface of a prior art electrophoresis plate were it not removed, and since the distribution of the liquid is irregular this would cause variations in the electric field at different regions of the electrophoresis plate. This in turn would undermine the accuracy of the analytical procedure because the electrophoresis plate would not be electrically homogeneous. On the other hand, as was noted above, removing the liquid by the usual expedient of blowing it away or blotting the electrophoresis plate increases the risk of contaminating or compromising the electrical integrity of the plate.

It is believed that the liquid forms thin pools or patches on the surface of a prior art electrophoresis plate when film 15 is removed due to surface forces at the interface between the electrophoresis medium and the liquid. Just as water forms beads on the surface of a newly-waxed car due to a different in the surface tension of the water and the surface tension of the wax, a difference in the surface tension of the electrophoresis medium and the liquid that is expressed by it causes the liquid to contract into pools upon removal of film 15 from a prior art electrophoresis plate. These pools are irregular in shape by nature. In accordance with the present invention, pooling of the liquid is avoided by adding a surfactant to control the surface tension of the expressed liquid with respect to the electrophoresis medium layer, so that the liquid does not pool but instead wets the surface of the electrophoresis medium in a uniform film even after film 15 is removed. The uniform film of liquid need not be removed prior to electrophoresis since it does not disrupt the homogeneity of the electrophoresis medium. The result is not only a reduced risk of erroneous results due to contamination of the electrophoresis plate, but also the elimination of a chore known to contribute to heterogenous plate surface phenomena.

A specific example of the fabrication of an electrophoresis plate 10 in accordance with the present invention will now be described.

Figure 3:
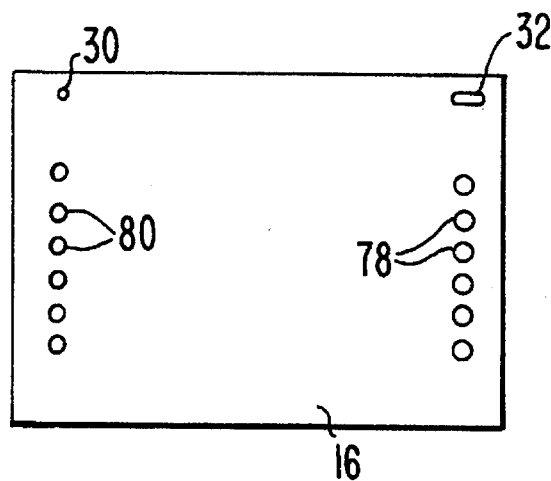
FIG. 3 is a top view of the substrate of the electrophoresis plate.
Figure 4:
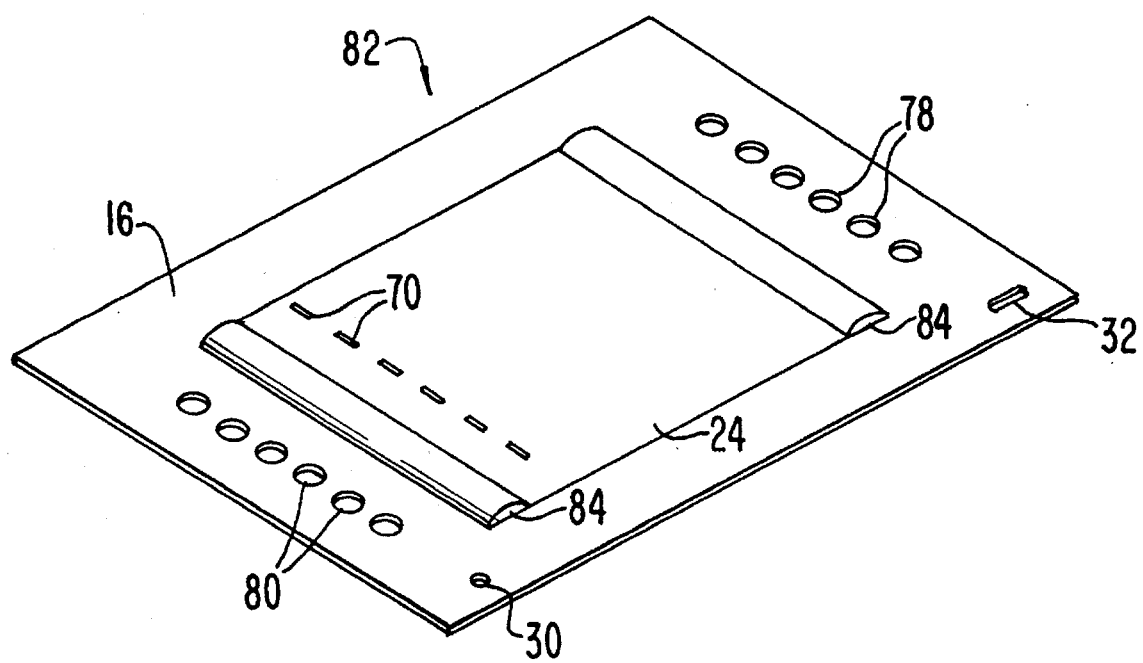
FIG. 4 is a perspective view illustrating an intermediate product formed by inserting the substrate into a mold and injecting a first mixture which includes a surfactant, the completed electrophoresis plate being produced from the intermediate product in a subsequent molding step.

FIG. 3 illustrates substrate 16, which is made of Mylar (trademark) plastic and has a gel fixed to it such as a thin priming film of agarose. The primed substrate is punched to provide alignment hole 30, alignment slot 32, six holes 78, and six holes 80. The substrate 16 is placed in a mold (not illustrated) and a first electrophoresis medium mixture is injected, thereby forming an intermediate product 82 as shown in FIG. 3. Intermediate product 82 includes the central portion 24 (see FIG. 1) of the electrophoresis medium layer, terminated at either end by rounded regions 84.

The first electrophoresis medium mixture is a thermosetting gel having the ingredients and relative amounts specified in the following Table:

TABLE 100 grams of water;
1.3 grams of agarose, which is available from FMC Corporation;
0.04 grams of sodium azide;
0.36 grams of trishydroxyaminomethane;
0.42 grams of sodium barbital;
0.1 grams of methyl cellulose, available from Dow Chemical Company under the designation "K-100LV Premium;"
0.1 grams of an anti-foaming agent that is available from DuPont under the designation "FG-10";
7.5 grams of sucrose; and
37 grams of ethylene diamine tetraacetic acid, or EDTA.

Of the above ingredients, the agarose imparts the microporous structure to the electrophoresis medium. The sodium azide acts as a bacteria inhibitor. The trishydroxyaminomethane and sodium barbital together act as a buffering agent, serving as an electrolyte to make the mixture conductive and adjusting the Ph of the electrophoresis medium to the desired value of 8.8. The sucrose provides humectant qualities, decreasing the vapor pressure and preventing evaporation. The EDTA is present to stabilize the gel. It is the methyl cellulose in this mixture which is a surfactant that serves to alter the surface tension of the liquid that is expressed beneath film 15 so that the liquid uniformly wets the electrophoresis medium layer when film 15 is removed.

The ingredients listed in the Table are mixed at 90° Centigrade. The mixture is then cooled above its gel point and injected into the mold (not shown) to form intermediate product 82.

As will be noted from the Table, in the preferred embodiment the ratio of the mass of the methyl cellulose employed to the mass of the water in the mixture is 0.1% (w/v). It is believed that different ratios, such as 3% (w/v) to 0.001% (w/v), would provide adequate surface active effect, depending on the surface tension of the gel. It is also believed that larger ratios could be used. What is needed is enough methyl cellulose to cause the liquid expressed under film 15 to uniformly wet the electrophoresis medium layer after film 15 is removed.

While methyl cellulose is the preferred surfactant, at least in an electrophoresis plate that is intended for assays of creatine kinase, other water-soluble celluloses such as ethyl cellulose and nitro cellulose can be used. In addition to such water-soluble celluloses, it is believed that povidones such as polyvinyl pyrrolidone can be used as a surfactant in an electrophoresis medium layer in order to make the liquid expressed under protective film 15 wet the electrophoresis medium in a uniform film after film 15 is removed. In general, non-ionic, zwitterionic, and cationic surfactants should work.

Intermediate product 82 is transferred into electrophoresis plate 10 by injection-molding a second gel mixture to form end regions 20 and 22. The second mixture need not include methyl cellulose. After the second mixture has gelled and electrophoresis plate 10 has been removed from the mold, it is mounted on container half 14, protective film 15 is applied to central portion 24, and container halves 12 and 14 are snapped together. The assembly is then hermetically sealed in a pouch (not illustrated).

The provision of holes 26, 28 in the electrophoresis medium layer 18 (and the apertures 78, 80 with substrate 16) accommodate the electrodes which extend upwardly from below the plate from the platform 34. When electrodes are positioned above the end portions 20, 22 of plate 10, the holes 26, 28 and apertures 78, 80 are not required but may be provided depending, inter alia, on the electrode configuration. Furthermore, the number of holes and the number of sample wells is illustrative only.

It will be understood that the above description of the present invention is susceptible to various modifications, changes, and adaptations, and the same are intended to be comprehended within the meaning and range of equivalents of the appended claims.

What is claimed is:

1. An electrophoresis plate, comprising:

a substrate;

an electrophoresis medium layer comprising agarose as a gelling agent with a substantially uniform thickness on the substrate;

a surfactant selected from the group consisting of povidones and water-soluble cellulose in an amount sufficient such that a liquid expressed from the electrophoresis medium layer forms a substantially uniform layer on said electrophoresis medium layer; and a removable film on the electrophoresis medium layer.

2. The electrophoresis plate of claim 1, wherein the surfactant is a water-soluble cellulose.

3. The electrophoresis plate of claim 2, wherein the water-soluble cellulose is methyl cellulose.

4. The electrophoresis plate of claim 2, wherein the amount of the water-soluble cellulose in the electrophoresis medium layer ranges from about 0.001% (w/v) to about 3% (w/v) of the amount of water in the electrophoresis medium layer.

5. The electrophoresis plate of claim 4, wherein the amount of the water-soluble cellulose in the electrophoresis medium layer is about 0.1% (w/v) of the amount of water in the electrophoresis medium layer.

6. The electrophoresis plate of claim 1, wherein the electrophoresis medium layer has a first and a second end portions and an intermediate portion;

said removable film being on said intermediate portion; and said end portions having a greater thickness than said intermediate portion.

7. An improved electrophoresis plate of the type which includes a substrate and an electrophoresis medium layer on the substrate and which is packaged with a removable film on the electrophoresis medium layer, the electrophoresis medium layer including a liquid and a gel in which the liquid is retained, removal of the film from the electrophoresis medium layer leaving liquid which has been expressed from the gel on the electrophoresis medium layer, wherein the improvement comprises:

the electrophoresis medium layer comprising agarose as a gelling agent;

wetting means in the electrophoresis medium layer for causing the liquid expressed from the electrophoresis medium layer to form a substantially uniform layer on the electrophoresis medium layer; and a removable film on the electrophoresis medium layer.

8. The electrophoresis plate of claim 7, wherein the wetting means is a surfactant selected from the group consisting of povidones and water-soluble cellulose.

9. The electrophoresis plate of claim 7, wherein the wetting means comprises a water-soluble cellulose.

10. The electrophoresis plate of claim 9, wherein the waters-soluble cellulose is methyl cellulose.

11. The electrophoresis plate of claim 10, wherein the amount of the methyl cellulose is about 0.001% (w/v) of the amount of water in the electrophoresis medium layer.

12. The electrophoresis plate of claim 7, wherein the electrophoresis medium layer has a first and a second end portions and an intermediate portion;

said removable film being on said intermediate portion; and said end portions having a greater thickness than said intermediate portion.

13. A method of making an electrophoresis gel plate package comprising the steps of:

providing a container having first and second portions;

providing an electrophoresis medium layer within said container first and second portions, said electrophoresis medium layer including a liquid and a gel in which the liquid is retained;

providing a wetting means in the electrophoresis medium layer in an amount effective for causing the liquid expressed from the electrophoresis medium layer to form a substantially uniform layer on said electrophoresis medium layer; and providing a removable film on the electrophoresis medium to retain the expressed liquid from the electrophoresis medium prior to electrophoresis.

14. The invention according to claim 13 wherein the wetting means is a water-soluble cellulose.

15. The invention according to claim 13 wherein the wetting means is methyl cellulose.

16. The invention according to claim 13 wherein the wetting means is methyl cellulose in an amount from about 0.001% to about 3.0% (w/v) of the amount of water in the electrophoresis medium layer.

17. The invention according to claim 13 wherein a substrate is provided on one side of said electrophoresis medium layer.

18. The invention according to claim 13 wherein the removable film is plastic.

19. An electrophoresis gel plate package comprising:

a container having first and second portions;

an electrophoresis medium layer positioned within said container portions, said electrophoresis medium layer including a liquid and a gel in which the liquid is retained;

wetting means in the electrophoresis medium layer in an amount effective for causing the liquid expressed from the electrophoresis medium layer to form a substantially uniform layer on said electrophoresis medium layer; and a removable film on the electrophoresis medium layer.

20. The invention according to claim 19 wherein the wetting means is a water-soluble cellulose.

21. The invention according to claim 19 wherein the wetting means is methyl cellulose.

22. The invention according to claim 19 wherein the wetting means is methyl cellulose in an amount from about 0.001% to about 3.0% (w/v) of the amount of water in the electrophoresis medium layer.

23. The invention according to claim 19 wherein the electrophoresis medium layer comprises agarose as a gelling agent.

24. The invention according to claim 19 wherein a substrate is provided on one side of said electrophoresis medium layer.

25. The invention according to claim 19 wherein the removable film is a plastic film.

26. The electrophoresis gel plate package of claim 19, wherein the electrophoresis medium layer has a first and a second end portions and an intermediate portion;

said removable film being on said intermediate portion; and said end portions having a greater thickness than said intermediate portion.

* * * * *